United States Patent
Beetz et al.

(10) Patent No.: US 6,544,171 B2
(45) Date of Patent: Apr. 8, 2003

(54) SYSTEM FOR PATIENT MONITORING

(75) Inventors: Klemens Beetz, Erlangen (DE); Michael Kraus, Forchheim (DE); Bernhard Lang, Feucht (DE); Martin Lang, Grossenseebach (DE); Axel Nagelschmidt, Erlangen (DE); Johannes Neudecker, Erlangen (DE); Jens Potschadtke, Erlangen (DE)

(73) Assignee: Biotronik Mess- und Therapiegerate GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/792,026

(22) Filed: Feb. 26, 2001

(65) Prior Publication Data

US 2001/0029321 A1 Oct. 11, 2001

(30) Foreign Application Priority Data

Feb. 25, 2000 (DE) .......................... 100 08 917

(51) Int. Cl.⁷ .............................. A61B 5/00; G08B 5/22; G08B 23/00; H04B 1/034
(52) U.S. Cl. .................... 600/300; 128/903; 340/573.1; 340/825.49; 455/95; 342/357.02
(58) Field of Search ................................ 600/300, 301; 607/32; 128/903, 904; 342/357.02, 357.06, 357.07, 357.08, 357.09, 359, 386, 387; 340/407.1, 407.2, 573.1, 573.4, 825.49; 455/456, 572, 574, 100, 95

(56) References Cited

U.S. PATENT DOCUMENTS

| 4,850,031 | A | * | 7/1989 | Allsop et al. ............ 340/573.1 |
| 5,164,652 | A | * | 11/1992 | Johnson et al. ............. 455/572 |
| 5,327,144 | A | * | 7/1994 | Stilp et al. .................. 342/387 |
| 5,652,570 | A | * | 7/1997 | Lepkofker ................ 340/407.1 |
| 5,720,770 | A |   | 2/1998 | Nappholz et al. |
| 5,963,130 | A |   | 10/1999 | Schlager et al. |
| 6,026,304 | A | * | 2/2000 | Hilsenrath et al. .......... 455/456 |
| 6,097,336 | A | * | 8/2000 | Stilp ...................... 342/357.02 |
| 6,195,559 | B1 | * | 2/2001 | Rapeli et al. ............... 342/359 |
| 6,236,836 | B1 | * | 5/2001 | Westman et al. ........... 455/574 |
| 6,292,698 | B1 | * | 9/2001 | Duffin et al. .................. 607/32 |

FOREIGN PATENT DOCUMENTS

| DE | 44 41 907 A1 | 6/1995 |
| DE | 295 14 982 U1 | 9/1996 |
| DE | 196 14 231 A1 | 10/1997 |
| DE | 197 07 681 | 5/1998 |
| DE | 197 31 986 A1 | 1/1999 |
| DE | 198 17 962 A1 | 10/1999 |
| DE | 198 44 296 A1 | 3/2000 |
| EP | 0 846 440 A2 | 6/1998 |
| EP | 0 963 734 A1 | 12/1999 |
| WO | WO 97/27499 A1 | 7/1997 |

* cited by examiner

Primary Examiner—Max F. Hindenburg
Assistant Examiner—David J. McCrosky
(74) Attorney, Agent, or Firm—Browdy and Neimark, P.L.L.C.

(57) ABSTRACT

A patient monitoring system (1) is provided with at least one body sensor (2a) for measuring a physiological parameter, as well as with a body signal processing unit (3) connected downstream from the former and/or a therapy device (2) designed to act on the patient (P), and a mobile radiotelephone end unit (7) operable in a cellular mobile radiotelephone network (1B) for transmitting data from the body signal processing unit or the therapy device to a central monitoring station (1C) and/or from the central monitoring station to the therapy device. A base station coordinate memory unit (13; 13') and a locator unit (12; 12.1' through 12.3') connected to the former serves for the rough determination of the location of the patient based on location information obtained from the current base station connection of the mobile radiotelephone end unit in the mobile radiotelephone network. For the fine position determination, a direction-finding transmitter (300) that sends out a direction-finding signal is provided in the mobile radiotelephone end unit (7). A separate direction-finding device (310) serves for the fine tracking of the direction-finding signal.

9 Claims, 2 Drawing Sheets

SYSTEM FOR PATIENT MONITORING

BACKGROUND OF THE INVENTION

1. Field of the Invention

The present invention relates to a patient monitoring system comprising at least one body sensor for detecting a physiological parameter, as well as, connected downstream from the body sensor, at least one of a body signal processing unit and a therapy device designed for acting on a patient, and a mobile radio end unit designed for transmitting data from at least one of the body signal processing unit and the therapy device to a central monitoring station, said mobile radio end unit being operable in a cellular mobile radiotelephone network having a multiplicity of preferably ground-based base stations, wherein a base station coordinate memory unit is provided and a rough locator unit for a rough determination of a patient's current location based on rough positioning information obtained from a current base station connection of the mobile radio end unit in tie mobile radiotelephony network.

2. Background Art

In cases of serious health impairments and/or after major surgery such as, for instance, after a heart transplant for an early detection of a possible rejection, it is advisable to provide for a long-term uninterrupted monitoring of the patient's condition. In view of the affected person's quality of life, but also for reasons of capacity and cost this should take place outside of a clinic.

For wearers of electromedical implants, such as cardiac packers, constant monitoring of the condition of the patient or device is necessary in some cases as well, and, as a rule, it is desirable to at least have the option to immediately signal a life-threatening condition of the patient or device along with a simultaneous determination of the patient's whereabouts.

A number of known systems for ambulatory patient monitoring exist for various applications.

In U.S. Pat. No. 5,626,630 A1, a medical telemetry system using an implantable quasi-passive transponder is described, which, in addition to the transponder, incorporates a relay device to be worn externally by the patient, and a remote monitoring station.

In DE 197 58 939 A1, a patient monitoring system is described whereby a patient device is automatically activated in response to a certain location of the patient for data transmission to a central monitoring station, in particular over a telephone network.

WO 97/00708 A1 describes an advanced, highly complex system for world-wide patient locating and data transmission from device implants to suitable analysis points. In order to determine the patient's geographic location based on the satellite positioning system GPS, the system incorporates a special receiver, which the patient carries with him.

The location of the patient is determined in the same complex manner with the cardiac stimulation system with expanded communication and monitoring options according to U.S. 5,720,770 A1, which in other respects also provides for the use of the fixed telephone network or of a cellular network for the transmission of relevant data.

In the applicant's German patent application 198 44 296.3, a patient monitoring and locating system is revealed that is operated with the assistance of a mobile radiotelephone end unit, on the basis of a cellular network, such as, e.g., the GSM network. The process entails a rough location determination with the aid of a base station coordinate memory unit and a rough locator unit connected to the former. The locating method used there is based on utilizing the location-relevant information that is constantly available internally in a cellular mobile radiotelephone network to determine the patient's location, forgoing separate means for geographic positioning.

This idea is based, on one hand, on the fact that the geographic coordinates of all utilized base stations are available at the mobile radiotelephone network operator's and that each registered end unit is, of course, located within the range of transmission and reception of at least one base station, however, normally within the range of multiple base stations at the same time. At the switching level of the mobile radiotelephone system, information is also available as to which base station it is, so that an approximate determination of the patient's location is possible based on the base station location data set alone.

Furthermore, in a modem mobile radiotelephone system, measurements of among others, the signal delay time take place at least to the base station that is currently active for the given end unit, so that the automatic handover can take place between different base stations, which means that a further piece of location-relevant information is present in the system, in the form of the signal delay time information. If the respective shortest signal delay times to multiple adjacent base stations are measured at the same time, their location data and corresponding signal delay time values may be used to obtain a very precise, two-dimensional determination of the location of the respective end unit and thus of the patient. Depending on the specific structure of the network, the signal delay time data may be queried at the end units or at the base stations, and optionally also at the switching level.

Lastly, the fact that the base stations, as a rule, operate with directional antennas principally offers a possibility to fine-tune the determination of the patient's location by determining and analyzing with which base station antenna the connection to the patient's end unit is maintained.

The above locating measures have the shortcoming—also in the case of signal delay time measurements—that the location resolution is within a magnitude of only ten to several hundred meters in dependence upon the cell size of the mobile radiotelephone network. This location resolution regarding the location of persons in an emergency situation is too rough to quickly locate the person in question in densely populated areas, such as inner city areas with multi-story multi-family homes or business offices and large crowds in which it is difficult to find a person, such as during big events. However, this analogously also holds true for very large mobile radiotelephone cells, for instance in the mountains or in the countryside.

SUMMARY OF THE INVENTION

To solve this problem, the invention now proposes, in addition to the rough location determination known from the prior art, to supplement the monitoring system with a three-dimensional fine locator unit incorporating, in the mobile radiotelephone end unit, a direction-finding transmitter that transmits a direction-finding signal, and a separate direction-finding device for the fine locating of the direction-finding signal, and thus of the mobile radiotelephone end unit, after the rough position determination.

Based on this configuration of the monitoring system, the mobile radiotelephone end unit of the monitored patient can be roughly located in the known manner when an emergency call is received, and an emergency response team can be dispatched to that location. This team is equipped with the direction-finding device and can, after arriving at the given location, switch the direction-finding transmitter of the mobile radiotelephone end unit of the monitored patient to a continuous send mode. Alternately, the direction-finding transmitter of the fine locator unit may also be turned on remotely by the operator of the mobile radiotelephone network himself. In other respects it is also advantageous in both cases if the direction-finding transmitter is formed by the transmitting portion of the mobile radiotelephone end unit itself.

The direction-finding device, too, is preferably formed by a modified standard mobile radiotelephone unit so that the fine locating may be implemented, for example, on the basis of the conventional GSM technology. This merely requires corresponding software adaptations in the operating programs of the mobile radiotelephone end units. The only relevant hardware addition that is then required, is to provide the mobile radiotelephone end unit with a direction-sensitive antenna which, in a standard mobile radiotelephone end unit, is a very simple process.

The fine locating on the basis of the direction-sensitive receive antenna may then lastly be perfected with a fine-resolution field strength indicator for the received direction-finding signal. Since the hardware technology of conventional GSM standard mobile telephones includes a field strength measuring device, this means that, again, only a software adaptation is required to implement a high-resolution numeric indicator in the display window of the end unit.

Advantageous improvement of the invention will, in other respects, be illustrated in greater detail below, in combination with the description of the preferred embodiment of the invention based on the figures.

Figure 1:
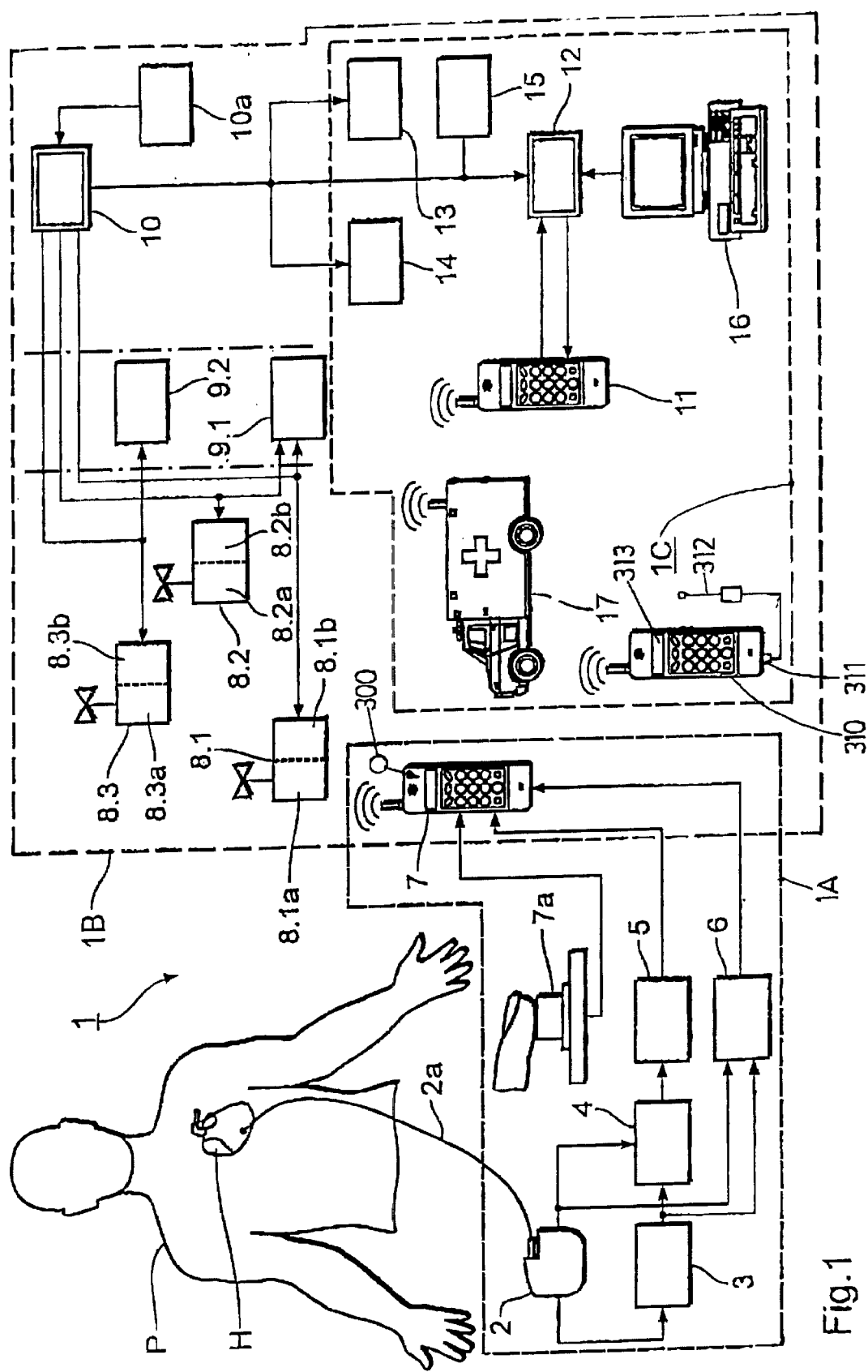
FIG. 1 shows a schematic diagram of a preferred embodiment of the overall system.

DESCRIPTION OF THE PREFERRED EMBODIMENT,

In FIG. 1, a patient monitoring system 1 is shown for monitoring and determining the location of a pacemaker patient P.

The patient P has a cardiac pacemaker 2 with an electrode lead 2a routed to the heart H forming the implanted portion of the system 1. The electrode lead 2a at the same time is also a sensor, for the cardiac activity as a physiological parameter, and a stimulation electrode. The implanted pacemaker 2 is connected via a telemetry connection known as such (not shown in the drawing) to a body signal processing unit 3 and, both directly as well as—via a second data route—through the body signal processing unit, to a parameter monitoring unit 4. The output of the parameter monitoring unit 4 has a switching unit 5 connected downstream. The pacemaker 2 and the body signal processing unit 3 are furthermore connected to an interface device 6. The interface device 6 is connected to a mobile telephone 7 via a data line, and the switching unit 6 is connected to the mobile telephone 7 via a control signal connection. This mobile telephone 7 is also assigned a manually operated on-switch 7a (which, in practice, will be formed by an appropriate function key on the cellular telephone itself). The above-named components form a patient unit 1A.

The mobile telephone 7 is, at the same time, an element of a GSM mobile radiotelephone network 1B that also encompasses a multiplicity of base stations, of which three adjacent base stations 8.1 through 8.3 are shown in the figure. They each comprise one base transceiver station (BTS) 8.1a, 8.2a, and 8.3a, respectively, as well as a base station controller (BSC) 8.1b, 8.2b, and 8.3b, respectively. At the level of the switching subsystem, in the example shown, the base stations 8.1 and 8.2 are assigned one and the same mobile switching center (MSC) 9.1 and the base station 8.3 is assigned a different MSC 9.2. All three base stations 8.1 through 8.3 have all assigned operation and maintenance center (OMC) 10. The distribution of functions between the BTS/PSC, the MSC and the OMC is specifically defined within the given system and does not require a general explanation here. The only prerequisite is that the OMC 10 has an assigned base station coordinate memory 10a, in which the geographic location data for all base stations of the network 1B is stored, and that the OMC is designed for central recording of the measured signal delay times and detected diversity allocations in the base stations. Lastly, the network 1B also includes a second mobile telephone shown in the figure, namely an end unit 11 assigned to a central patient monitoring station 1C.

The core element of the central patient monitoring station 1C is a central computer 12, which is connected bi-directionally to the end unit 11 (which, in this example, symbolically stands for a multiplicity of end units required in practice) and which is also connected on the input side to the OMC 10. Also assigned to the central computer 12 are a coordinate buffer memory 13, a signal delay time buffer memory 14f for the measured signal delay time values, an antenna allocation buffer memory 15 for the detected antenna allocations of the base station(s) with respect to the end unit 7, and a multiplicity of PC work stations, for which, again, only a PC 16 is shown symbolically. Lastly, the central patient monitoring station is assigned emergency response personnel, which are symbolized in the figure by the ambulance 17 and which, although this is not shown in detail for reasons of clarity, can also be activated via the mobile radiotelephone network 1B.

Figure 2:
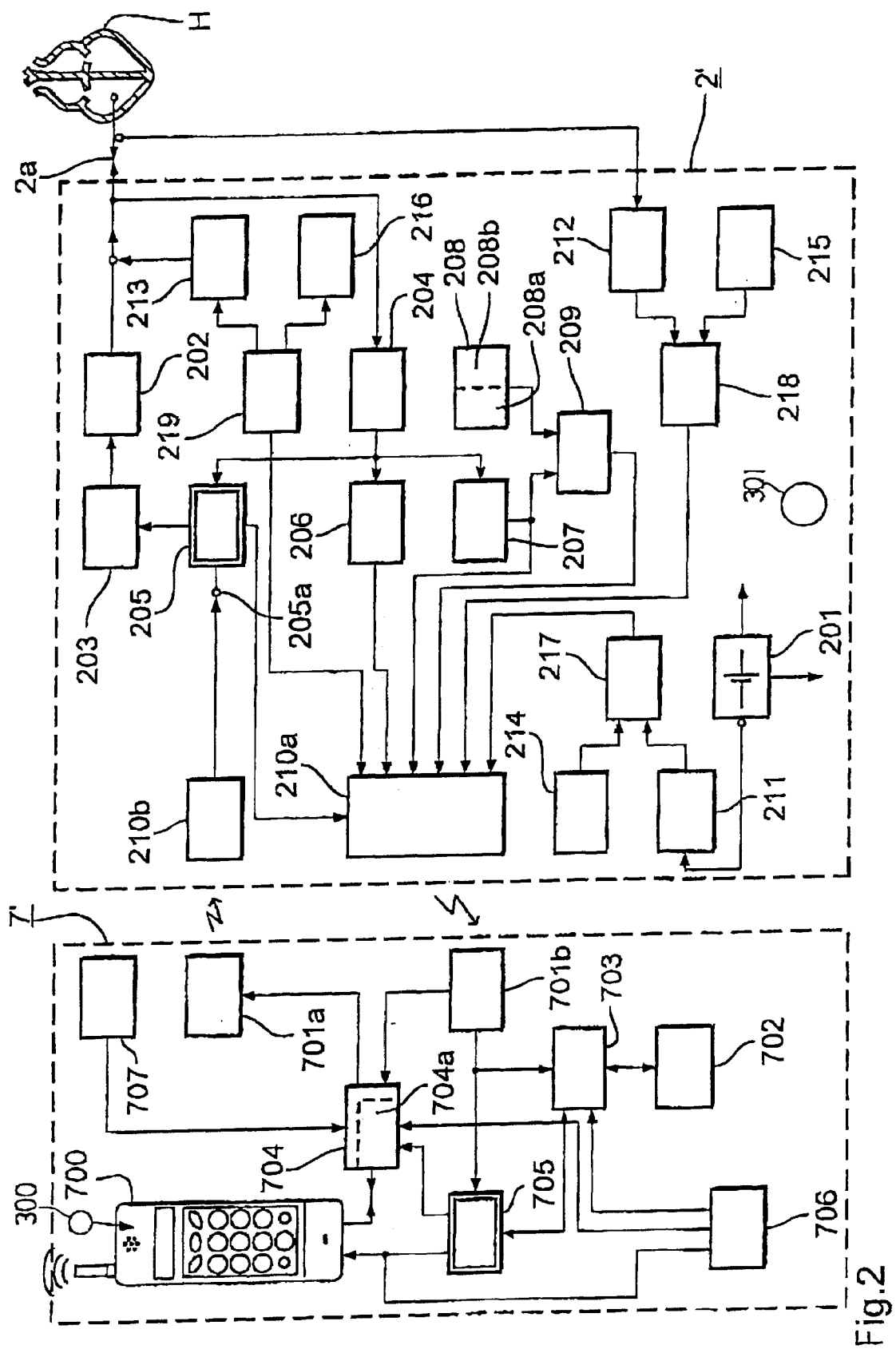
FIG. 2 shows a simplified operation block diagram for the components on the patient side in a modified system according to FIG. 1.

FIG. 2 is a simplified operation block diagram of the part 1A' of a patient monitoring system modified from FIG. 1, showing only the operational components that are essential for the explanation of the embodiment of the invention. Here, in contrast to the schematic illustration in FIG. 1, the body signal processing unit and the operational elements that are part of the parameter monitoring unit are integrated into the pacemaker itself.

The cardiac pacemaker 200 furthermore has a largely known design and is of a type that permits at least a ventricle stimulation as well as the detection of ventricular cardiac signals. For this purpose it includes a battery 201 for power supply, a stimulation pulse generator 203 that is connected via an output stage 202 on the output side to the ventricle electrode 2a placed in the ventricle of the heart H, as well as an input stage 204 connected to the electrode 2a on the input side. In the figure the pacemaker control functions have been grouped together in the control block 205, which has programming inputs 205a for external programming of the pulse rate and amplitude and for activating supplemental functions, such as tachycardia determination pulse sequences.

Provided downstream from the input stage 204 (beside the control block 205) are an intermediate cardiac signal memory 206 and a heart rate determination stage 207, in which detected cardiac signals (intercardial electrograms, IGEM) are stored temporarily and furthermore processed for determining the current heart rate. The pacemaker 2' furthermore incorporates a rate threshold memory 208 with memory areas 208a and 208b for an upper and lower rate threshold value, respectively, and a rate comparator 209 connected to the memory 208, as well as to the heart rate determination stage on the input side, On the output side, both the intermediate heart signal memory 206 as well as the heart rate determination stage 207, as well as the rate comparator 209 arc connected to a telemetry transmitter unit 210a on the pacemaker side.

The pacemaker battery 201 has assigned to it, in a manner known per se, a battery condition detection unit 211, and the output stage 202 has an assigned electrode impedance detection unit 212 and a pulse amplitude detection unit 213, which are also known per se. The detector units 211 through 213 each have assigned to them or connected downstream from them, threshold memories 214 for the battery voltage, 215 for the electrode impedance, and 216 for the pulse amplitude, and one comparator unit 217 through 219 each. The outputs of the comparator units 217 through 219 are connected to the telemetry transmitter unit 210a. A telemetry receiver unit 210a on the pacemaker side is connected to the programming inputs 205a of the control block 205. The telemetry units 210a, 210b on the pacemaker side—like the external units (see further below)—are designed for far-range telemetry with a range of 1 to 2 meters.

An external patient device 7' incorporates a mobile telephone 700 with a largely customary design in the structure of a GSM module and a send and receive unit 701a, 701b, implementing (together with the implanted transmitter and receiver unit 210b and 210a) a bi-directional telemetry path to the cardiac pacemaker. It furthermore incorporates a buffer memory 702 and memory access control 703 assigned to the same for intermediate storage of the data received via the telemetry path and an interface (such as a PCMCIA card) 704 supporting the transfer protocol of the given mobile, radiotelephone network and having an encoding unit 704a, for connection to the cellular phone part 700 and conversion of the data formats of the data to be transmitted to the central patient monitoring station 1C (FIG. 1) and programming data received from the same.

Lastly, the patient device incorporates a control stage 705 for automatic control of an emergency call, which is connected on the input side to the telemetry receiver unit 701b, on the output side to the telephone unit 700 and interface 704, as well as on the input and output side to the memory access control 703. Lastly, a manually operated emergency call switching unit 706 is provided for manual activation of an emergency call, which is also connected to the telephone unit, the memory access control and the interface. An identification data memory 707 that is connected to the interface 704 contains non-variable device and patient identification data.

The actual core of the present invention will now be discussed in greater detail with reference to the two embodiments according to FIGS. 1 and 2. The mobile telephones 7, 700 are equipped with a special function. In fact, a direction-finding transmitter 300 is integrated into the mobile telephones that can be activated based on a remote control that will be described in detail further below. When activated, this direction-finding transmitter 300 transmits, in a continuous send mode, a direction-finding signal that lies on a GSM-based frequency. The direction-finding transmitter 300 may thus be formed by the transmitter part of the mobile telephone 7, 700 itself. An intermittent fixed frequency signal is transmitted for locating the mobile telephone 7, 700 by means of a direction-finding device that will also be explained in detail further below. The strength of this signal is to be adjusted according to the remaining battery capacity for the energy supply to the mobile radiotelephone end unit 7, 700. Also, the repeat rate of the intermittent fixed frequency signal must be adjusted according to the remaining capacity of the energy supply for the mobile telephone 7, 700 in such a way that a sufficiently strong and sufficiently often repeated signal is transmitted on one hand, but a certain minimum operating time is still ensured on the other hand.

To accomplish the inventive fine position determination, a direction-finding device 310 cooperates with the direction-finding transmitter 300, the direction-finding device 310 again being—as indicated in FIG. 1—a mobile telephone. The direction-finding device 310 in the form of a modified standard mobile telephone may be connected via the external antenna connector 311 to a direction-sensitive receive antenna 312 that serves to find the direction of the signal transmitted by the direction-finding transmitter 300. For a precise indication of the direction in which the direction-finding transmitter 300 is located relative to the direction-finding device 310, the software technology of the latter is modified in such a way that the telephone display implements a high-resolution field-strength display 313 for the received direction-finding signal.

The relevant inventive aspects of the operation of the embodiment according to FIGS. 1 and 2 will be explained below; details of the pace maker functions (including the telemetry function) as well as of the data transmission in a mobile telephony network shall be deemed known from the prior art. In the following it will also be assumed that, in addition to means for the data transmission, the mobile radiotelephone path also has a speech channel in the usual manner.

During the ongoing operation of the pacemaker 2 or 2', respectively, the heart rate is permanently monitored via the body signal processing unit 3 or—in the specific example of FIG. 2—via the heart rate determination stage 207, the rate threshold memory 208 and the rate comparator 209, and the function of tie pacemaker is monitored via the parameter monitoring unit 4—according to FIG. 2 via the stages 211 through 219, specifically regarding battery voltage, pulse amplitude and electrode impedance. If it is found as a result of a threshold comparison, that a relevant measuring parameter has exceeded the permissible range, the mobile telephone 7 is immediately activated by the signal indicating this circumstance, in the embodiment shown in FIG. 1 by the switching device 5. The sequence of events includes the automatic activation of the telephone, dialing of a preprogrammed (in an internal, not separately shown memory of the telephone unit) emergency number and sending of a data string stored in the pacemaker 2 via the interface 6 after a connection has been established.

In the modified embodiment according to FIG. 2, the telemetry transmitter unit 210a is automatically activated by an output signal of one of the comparator units 209, 217, 218 or 219 reflecting an unacceptable value for one of the monitored parameters. This telemetry transmitter unit 210a subsequently transmits, controlled by the control block 205, to the external patient unit 7' an activation signal as well as a preset (primary) data string encompassing specifically the IEGM read out from the heart signal memory 206 and the current value of the heart rate available at the output of the heart rate determination stage 207.

There, the activation signal and the data string are received by the external telemetry receiver unit 701*b* and routed to the external control stage 705, and the primary data string is initially—controlled by the control string and the memory access control 703—stored in the external buffer memory. After the mobile telephone 700 has been switched on and a connection to the contacted end unit 11 at the central patient monitoring station IC has been established, the data string is read out from the buffer memory and supplemented with identification data from the identification memory 707 to form a secondary data string, which is encoded in the encoding unit 704*a* and sent to the patient monitoring center as an emergency call.

There, the emergency call is received by the mobile telephone 11 and the data sting is routed to the central computer 12 and forwarded from there to a PC work station 13 where a cardiologist on duty can now perform an immediate evaluation to analyze the emergency and determine the required emergency measures.

Simultaneously with the data analysis, the determination of the location of the emergency patient takes place based on the registration of his mobile telephone 7 or 700 with one or more of the base stations 8.1 through 8.3 of the GSM network IB, as well as based on an analysis of the signal delay time and optionally of the antenna allocation data determined in the system. The geographic data of the actively connected base station and those of the BTC adjacent to the same for which signal delay time measurement data are available, are read from the memory 10*a* at the OMC 10 into the coordinate buffer memory 13. The available signal delay time data—optionally in their time-dependence over a predetermined length of time—are taken over into the long-term buffer memory 14. The data, which represent through which one of the directional antennas of the base station the connection or signal delay time measurements have taken place, are loaded into the diversity memory 15. The central computer 12 accesses the content of these memories and calculates, based on known navigational algorithms, the rough location of the mobile telephone 7 of the emergency patient.

If the evaluation of the transmitted data has resulted in the necessity for an emergency response, the emergency personnel 17 are provided with the rough location information and result of the evaluation and can be on their way to the patient.

As soon as the emergency response personnel 17 have reached the previously determined rough location of the patient, the direction-finder device carried by them in the form of the mobile telephone 310 activates the direction-finding transmitter 300 in the patient's mobile telephone 7, 700. This direction-finding transmitter 300 transmits the direction-finding signal, which is detectable with the aid of the direction-finding device 310. The fine location of the patient P can thus be reliably determined and he can be found quickly and reliably even in areas in which it is difficult to find a person.

As an alternative in the "fine search" for the patient, the option may be provided that the direction-finding transmitter 300 is activated not by the emergency response personnel 17 but by the operator of the mobile radio-telephone network 1B. An appropriate evaluation system for the direction-finding signals received from the direction-finding device 310 may be located there as well, so that the emergency response personnel 17 may be directed toward the patient P via the direction-finding device 310 by the mobile network operator by voice commands. For this purpose the direction-finding device 310 may be operable in a dual mode, in which a direction-finding mode alternates with a message transmission mode.

Lastly, it needs to be pointed out that, in addition to the direction-finding transmitter 300 in the mobile telephone 700, the pacemaker 2' itself may be equipped with an emergency direction-finding transmitter 301, which can be activated if the patient P with his pacemaker 2' and the external patient device 7' should accidentally become separated.

What is claimed is:

1. A system (1) for patient monitoring comprising:

at least one body sensor (2*a*) for detecting a physiological parameter; p1 at least one body signal processing unit (3; 204, 206) connected with the body sensor (2*a*) and a therapy device (2; 2') adapted to act one a patient (P);

a central monitoring station (1C) being connected to a cellular mobile radiotelephone network (1B) by a terminal unit (11);

a portable mobile radio terminal unit (7; 700) which transmits data from the body signal processing unit (3; 204, 206) and the therapy device (2; 2') to the central monitoring station (1C) by the cellular mobile radiotelephone network (1B), a base station co-ordinate memory unit (13) in the central monitoring station (1C) storing base station coordinates of base stations (8.1; 8.2; 8.3) of the cellular mobile radiotelephone network (1B);

a rough locator unit (12) in the central monitoring station (1C) for a rough determination of a patient's current location based on rough positioning information obtained from said base station coordinates of a current base station connection of the mobile radio terminal unit (7; 700) in the cellular mobile radiotelephone network (1B);

a fine locator unit comprising a direction-finding transmitter (300) in the mobile radio terminal unit (7, 700) emitting a direction-finding signal and a separate, portable direction-finding receiver (310) for fine tracking of said direction-finding signal and fine locating the mobile radiotelephone terminal unit (7, 700) after the rough location determination, wherein the direction-finding transmitter (300) that transmits a direction-finding signal is formed by a transmitter part of the mobile radio terminal unit (7, 700) itself, wherein the direction-finding receiver is formed by a modified standard mobile radio terminal unit (310), and a high-resolution field intensity meter (313) for the direction-finding signal to be received.

2. A monitoring system according to claim 1, wherein the direction-finding transmitter (300) is switchable by remote control by an operator of the direction-finding receiver (310) into a continuous transmission mode.

3. A monitoring system according to claim 1, wherein the direction-finding transmitter (300) of the fine locator unit is activated remotely by an operator of the cellular mobile radiotelephone network (1B).

4. A monitoring system according to claim 1, wherein the direction-finding transmitter (300) transmits an intermittent fixed-frequency direction-finding signal.

5. A monitoring system according to claim 4, wherein at least one of a transmitter power and a repeat rate of the intermittent fixed frequency signal is adjustable in dependence upon a remaining capacity of an energy supply to the mobile radio terminal unit (7, 700).

6. A monitoring system according to claim 1, wherein the direction-finding receiver (310) is equipped with a direction-sensitive receiving antenna (312) for the direction-finding signal.

7. A monitoring system according to claim 6, wherein the direction-sensitive receiving antenna (312) is connected via an external antenna connector (311) of a standard mobile radio terminal unit (310).

8. A monitoring system according to claim 1, wherein the mobile radio terminal unit (31) functioning as the direction-finding receiver is operable in a dual more operation in which a direction-finding mode alternates with a message-transmission mode.

9. A monitoring system according to claim 1, wherein an additional direction-finding transmitter (301) is integrated into the therapy device (2') adapted to act on the patient (P).

* * * * *